United States Patent [19]

Allen et al.

[11] Patent Number: 5,423,989
[45] Date of Patent: * Jun. 13, 1995

[54] PLASMA FORMING DEVICE

[75] Inventors: Michael P. Allen, Sunnyvale; Robert B. Shibuya, Los Altos, both of Calif.

[73] Assignee: Chemtrack, Inc., Sunnyvale, Calif.

[ * ] Notice: The portion of the term of this patent subsequent to Jan. 22, 2008 has been disclaimed.

[21] Appl. No.: 6,597

[22] Filed: Jan. 21, 1993

Related U.S. Application Data

[63] Continuation-in-part of Ser. No. 765,046, Sep. 24, 1991, abandoned, which is a continuation-in-part of Ser. No. 357,045, May 24, 1989, abandoned, which is a continuation-in-part of Ser. No. 324,407, Mar. 16, 1989, Pat. No. 4,987,085, which is a continuation-in-part of Ser. No. 195,881, May 19, 1988, Pat. No. 4,999,287.

[51] Int. Cl.$^6$ .............................................. B01D 61/00
[52] U.S. Cl. .............................. 210/650; 210/488; 210/489; 210/490; 210/505; 210/508; 210/645; 210/651; 210/767; 210/800; 210/806; 422/101; 436/177; 436/178
[58] Field of Search ................ 210/641, 645, 650, 651, 210/767, 800, 806, 488, 489, 490, 505, 508; 436/174, 169, 175, 177, 178, 807, 808, 825; 530/354, 356, 357; 422/56, 58, 61, 101

[56] References Cited

U.S. PATENT DOCUMENTS

| | | | |
|---|---|---|---|
| 3,663,374 | 5/1972 | Moyer et al. | |
| 3,992,158 | 11/1976 | Przybylowicz et al. | 422/58 |
| 4,256,693 | 3/1981 | Kondo et al. | 422/56 |
| 4,477,575 | 10/1984 | Vogel et al. | 436/170 |
| 4,810,394 | 3/1989 | Masuda | 210/767 |
| 4,816,224 | 3/1989 | Vogel et al. | 422/55 |
| 4,824,639 | 4/1989 | Hildenbrand et al. | 422/56 |
| 4,845,132 | 7/1989 | Masuoka et al. | 210/490 |
| 4,876,067 | 10/1989 | Deneke et al. | 422/56 |
| 4,987,085 | 1/1991 | Allen et al. | 436/169 |
| 4,999,287 | 3/1991 | Allen et al. | 435/11 |
| 5,084,173 | 1/1992 | Nitadori et al. | 210/490 |
| 5,130,258 | 7/1992 | Makino et al. | 436/169 |
| 5,215,886 | 6/1993 | Patel et al. | 436/71 |
| 5,266,219 | 11/1993 | Pall et al. | 210/767 |

FOREIGN PATENT DOCUMENTS 1-127959 5/1989 Japan .

OTHER PUBLICATIONS

Allen, et al. (1990), "A noninstrumented quantitative test system and its applicationfor determining cholesterol concentration in whole blood," Clin. Chem. 36(9):1591–1597.

Glick and Ryder (1987), "analytical systems ranked by freedom from interferences," Clin. Chem. 33(8)1453–1458.

Primary Examiner—John Kim
Attorney, Agent, or Firm—Bertram I. Rowland; Bret E. Field

[57] ABSTRACT

Devices are provided for producing plasma or serum from blood samples, where the plasma or serum is substantially free of red blood cells, hemoglobin, and metabolites and degradation products thereof. The sample can be used in various assays without interference from the interfering components of red blood cells.

2 Claims, 1 Drawing Sheet

U.S. Patent — June 13, 1995 — 5,423,989
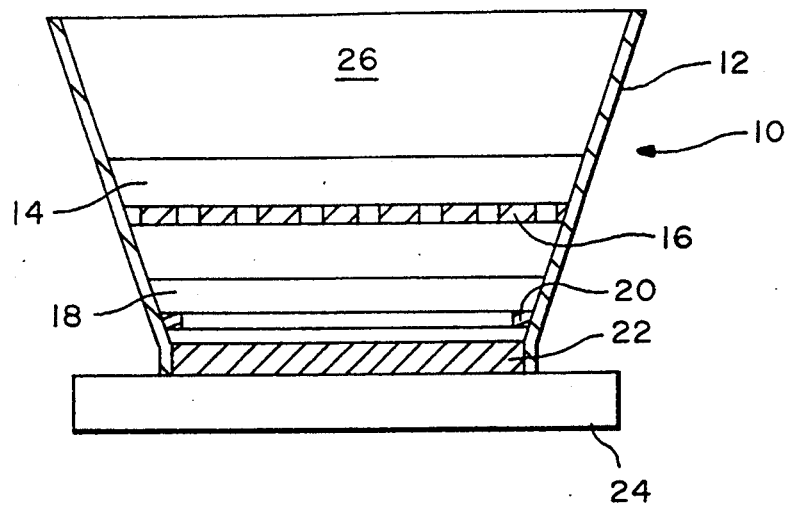
FIG.—1
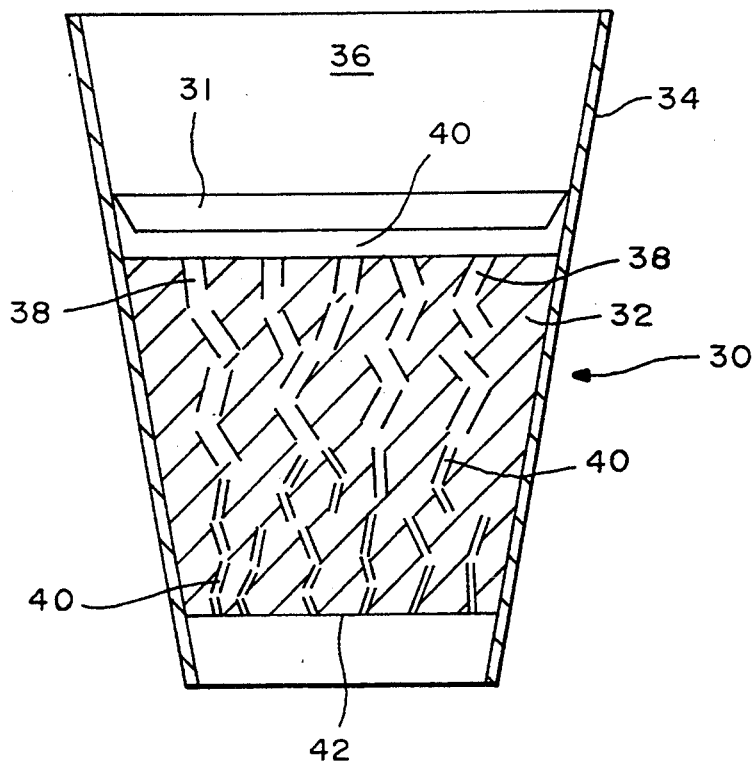
FIG.—2

PLASMA FORMING DEVICE

CROSS-REFERENCE TO RELATED APPLICATIONS

This application is a continuation-in-part of application Ser. No. 765,046, filed Sep. 24, 1991, now abandoned which is a continuation-in-part of application Ser. No. 357,045, filed May 24, 1989, now abandoned which is a continuation-in-part of application Ser. No. 324,407, filed Mar. 16, 1989, now U.S. Pat. No. 4,987,085, which is a continuation-in-part of application Ser. No. 195,881, filed May 19, 1988, now U.S. Pat. No. 4,999,287, which disclosures are incorporated herein by reference in their entirety.

INTRODUCTION

1. Technical Field

The field of the subject invention concerns providing red-blood-cell-free fluid samples from blood for use in assays.

2. Background

There is substantial interest in developing assays where blood may be directly used as the sample. Particularly, where one is interested in assay devices for use in doctors' offices and homes, it is undesirable to require that the doctor's assistant or patient be required to measure the sample, isolate serum or plasma from blood, dilute the sample to an appropriate concentration, and then carry out the assay. Therefore, there has been interest in developing devices which will independently perform the various steps involved in the assay.

Where blood is the sample, the presence of red blood cells (RBC's) can interfere with the ability to determine a colored signal. The various components of the red blood cell which provide the deep red color, will become dispersed in the assay medium upon lysis of the cells resulting in discoloration of the assay medium. The hemoglobin and other cell components can interfere with the assay chemistry. The color-forming materials from the RBC's will then interfere with the accurate detection of a signal. Therefore, whole blood is rarely used as the sample, the blood usually being treated to separate the RBC's. Where the device is substantially automatic, it is necessary that there be a simple automatic way to provide for a red-blood-cell-free sample from blood. However, the red blood cells are susceptible to lysis, so that it is not only necessary to remove the red blood cells, but to provide ways which do not result in the lysis of the red blood cells, but efficiently remove the red blood cells and provide a plasma or serum sample.

RELEVANT LITERATURE

German Patent No. 22 22 951 describes a filter assembly containing chemical reagents for removing cells from blood and measuring CPK. U.S. Pat. Nos. 4,477,575 and 4,816,224 describe the use of a glass fiber layer having a defined density for producing plasma or serum from blood. Allen, et al., *Clin. Chem.* 36/9, 1591–1597 (1990) describes a filter device employed in the subject invention.

SUMMARY OF THE INVENTION

Devices are provided which allow for the efficient production of serum or plasma from blood, as well as being sample volume independent, employing a membrane system comprising a first coarse membrane layer, preferably coated with a fibrous protein, and a second fine membrane layer, whereby red blood cells are efficiently removed without significant lysis of the red blood cells, so as to provide a substantially red-blood-cell- and hemoglobin-free sample.

BRIEF DESCRIPTION OF THE DRAWINGS

FIG. 1 is a diagrammatic view of a device having two independent membranes with relatively uniform pore size; and FIG. 2 is a diagrammatic view of a device having two membranes, one membrane having two different regions of different pore size.

DESCRIPTION OF THE SPECIFIC EMBODIMENTS

Devices are provided for use in assays, where a blood sample is to be employed for the detection of an analyte. Specifically, the devices provide for the efficient removal of red blood cells, without lysing of the blood cells, so as to provide a serum or plasma sample substantially free of interfering red blood cells or hemoglobin or metabolic or degradation products thereof. The device will normally be a part of a sample receiving structure, where the sample will pass through the device and be received by a bibulous member, capable of absorbing the serum or plasma which passes through the device.

The blood sample will normally be one or a series of small drops, generally having a total volume under about 250 $\mu l$, more usually from about 10–100 $\mu l$. The layers through which the sample flows may include a mesh layer, and will include a first membrane, and a second membrane cooperating with the first membrane to ensure the substantially complete removal of any interfering cells from the blood sample. The first membrane or depth filter may have 1, 2 or several layers of like or different material. The first membrane is composed of any depth filtration medium, including but not limited to glass filters, synthetic fibers, metal fibers, ceramic fibers, natural fibers, or the like. (By "depth filter" is intended a system for removing particulates.)

The first cellular separation member is used to reduce the concentration of red and white blood cells received by the second filtration member, which has a smaller pore size. By lowering the red blood cell content by from about 10 to 90%, usually from about 30 to 90% of the original red blood cell content, with the first membrane member, the second member is able to efficiently and accurately remove at least substantially all of the red blood cells from the blood sample. Since the first membrane acts as a coarse separation means, the first membrane may take any of a wide variety of forms.

Various packagings or sieving depth filters may be employed, such as glass fibers, cellulose filters treated with red blood cell capture reagents, glass fiber filters, or synthetic fiber filters. Glass fiber filters are available from such manufacturers as Whatman, Schleicher and Schuell, MSI, and Pall. The glass fiber filters are further characterized by a glass fiber diameter in the range of about 0.5–9$\mu$, and a density of about 40 to 200 g/m$^3$, the thickness for the different filters being from about 0.15 mm to 1 mm. The glass fiber filters may be illustrated by S&S Glass 30, Whatman GF/D, and S&S 3662. The normal pore size will usually be in the range of about 1 to 20$\mu$, but particulates, including cells, within this range may not be retained.

The filter may be treated with a coating agent to reduce hemolysis, particularly when a glass fiber filter is used. A solution from about 0.01 to 5% fibrous protein by weight, preferably about 0.1 to 1% by weight, that will coat a filter, and not interfere with the sample or assay, is a suitable agent. Such fibrous proteins include, but are not limited to, keratins, collagens and gelatin. The reduction of hemolysis will vary with the specific choice of protein. The use of gelatin is preferred when there is a possibility that the glass fibers will be mechanically crushed.

Other coarse separation membranes may include cellulosic membranes, e.g., filter paper, to which red blood cell binding proteins or agglutination agents are immobilized. Such proteins may include lectins, antibodies specific for RBC surface proteins, thrombin, ion exchange agents, etc. The preparation of such filters by conjugating proteins or other agents to cellulose is well known. Cellulose may be activated in a wide variety of ways employing carbodiimide, carbonyl diimidazole, cyanogen bromide, chloroacetic acid, where the acid may then be activated with carbodiimide, or the like. The literature is replete with examples of binding of proteins to cellulosic membranes for a variety of reasons, which techniques may be employed here. Multiple layers of coarse separation membranes may be employed.

Immediately beneath the first membrane will be the second membrane, which will be in fluid receiving relationship with the first membrane, either in contact with the first membrane or in close proximity thereto. Generally, the spacing between the first and second membranes will not exceed a distance which inhibits fluid flow, so that fluid readily flows from the first to the second membrane. The non-asymmetric (symmetric) membranes which are employed will be those in the medium porosity range, having an average porosity in the range of about $0.2\mu$ to $7\mu$, preferably about 0.2 to $2\mu$, where the pores may or may not be of substantially uniform diameter through the membrane. By contrast, where an asymmetric membrane is employed, that is the diameter of the pores vary from one surface to the other, desirably the membrane will have a minimum porosity not less than about $0.2\mu$, preferably not less than about $0.45\mu$, and the maximum porosity will generally not exceed about $40\mu$, more usually not exceed about $20\mu$. Illustrative microporous membranes which may find use include Filterite polysulfone asymmetric, $20\mu$-$0.45\mu$, Sartorious cellulose acetate, $1.2\mu$, Nucleopore, etc.

The choice of the second membrane is important, since the amount of red blood cell lysis is dependent on a number of factors. Depending on the size of the pores, the amount of lysis will greatly vary. Since lysis results in release of colored cell components, which can interfere with detection of a signal on a measuring strip and act to decompose hydrogen peroxide, where hydrogen peroxide is involved in producing a colored signal, merely removing cells is insufficient. The filters, particularly if glass, may be coated to reduce the amount of hemolysis. A further consideration is the pressure differential across the membranes. Again, the appropriate choice of membranes will affect the pressure drop and forces acting on the cells, where the pressure differential can affect the stability of the cells.

Thus, the two membranes serve to act together to efficiently and accurately remove red blood cells from the blood sample with little, if any, hemolysis, so as to provide a plasma or serum sample which may be accurately analyzed without interference from hemolytic products, such as heme. Also, as distinguished from the prior art and membrane systems for removal of RBC's, the operation of this subject device is substantially independent over a relatively wide sample volume range. In particular, the device operation is independent of sample volume for samples which range from 10–500 $\mu$l in volume. In this way, one need not be concerned about careful measuring of the sample volume, since an increased volume will not result in RBC interference.

The sample receiving element will be immediately beneath the red blood cell removing membranes and in fluid receiving relationship with the membranes. The sample receiving element will normally be a bibulous member able to absorb the fluid. Various bibulous materials may be used, such as cellulosic materials, e.g., paper, or the like. The sample receiving element will usually be of a size in the range of 5 to 100 $mm^2$ surface area and a thickness in the range of about 0.1 to 2 mm, having a volume capacity of from about 1 to 30 $\mu$L. The sample receiving element may be round, square, rectangular, quadrilateral or polygonal.

The subject device may be used as described in application Ser. No. 195,881, filed May 19, 1988, now U.S. Pat. No. 4,999,287 or the device in U.S. Pat. No. 4,959,324.

For further understanding of the invention, the figures will now be considered. In FIG. 1, the device 10 has a holder 12 which supports two coarse membranes 14 and 16. As already indicated, the coarse membranes may be of any convenient material, where the pore size is preferably in the range of about 1 to $20\mu$. The finer membrane 18 is supported by ring 20 and is spaced close enough to coarse membrane 16, so that flow from first coarse membrane 14 can readily occur through second coarse membrane 16 to finer membrane 18. In fluid receiving relationship with finer membrane 18 is bibulous sample receiving element 22 on support 24. Thus, the sample is placed in well 26 where it passes through coarse membranes 14 and 16, where a substantial portion of the red blood cells are removed, the partially-RBC-freed blood then being further filtered by finer membrane 18, where substantially all of the red blood cells are removed. The red-blood-cell-free serum or plasma is then absorbed by the bibulous receiving element 22, which may then be used in any convenient manner. Of course, one need not have a bibulous member as a sample-receiving element, the resulting plasma or serum may be used in any manner, being diluted in an assay medium or otherwise employed.

In FIG. 2 is indicated a device employing an asymmetric membrane. In the asymmetric membrane, the pores vary in diameter as one proceeds down the membrane. This is roughly diagrammatically depicted in FIG. 2. The device 30 has coarse membrane 31 and asymmetric membrane 32 in container 34 with well 36. Large pores 38 intersect the upper surface of the membrane 32. As one proceeds through the asymmetric membrane 32, one encounters smaller pores 40 which connect with the larger pores 38 and the lower surface 42 of the asymmetric membrane 32. As previously indicated, the porosity across the membrane will generally be in the range of about 0.4–$40\mu$. The blood sample is introduced in the well 36 and will proceed through the membrane 32, where red blood cells will be removed without any significant lysis.

The following examples are offered by way of illustration and not by way of limitation.

EXPERIMENTAL

I. A microporous membrane (Filterite polysulfone asymmetric, 20μ–0.45μ, or Sartorious cellulose acetate 1.2μ, Nucleopore or a nylon mesh screen (Nitex, 3-325-58) were laminated to two Mylar members, spaced apart, to leave an opening over the membrane. A 3×5 mm gap between the Mylar film was provided with the membrane or screen side down, glass fiber filters were layered above the gap. Immediately above the gap was a 3×5 mm piece of S&S glass 30, upon which was placed a 7×5 mm piece of Whatman GF/D (GF=glass fiber) fiber filter. The total water absorbance capacity of the filters in this configuration is 42 μL. The filters were held in place with 3M booktape (Scotch 845), joining the upper filter and each Mylar member.

A summary of the three devices compared in this experiment are:

| Device Type | Components |
|---|---|
| I. Gradient Membrane | Layer 1 - Glass Fiber Whatman GFD |
| | Layer 2 - Glass Fiber S&S 30 |
| | Layer 3 - Filtrite Asymmetric Membrane 0.45–20 μm |
| II. Symmetric Membrane | Layer 1 - Glass Fiber Whatman GFD |
| | Layer 2 - Glass Fiber S&S 30 |
| | Layer 3 - Cellulose Acetate Membrane 1.2 μm |
| III. Nylon Mesh without Membrane | Layer 1 - Glass Fiber Whatman GFD |
| | Layer 2 - Glass Fiber S&S 30 |
| | Layer 3 - Nylon Mesh |

The complete assembly was situated in contact with a 5×5 mm S&S paper filter on a plexiglass board, so that the membrane contacted the paper. The assembly was held fast with a nylon mesh screen.

Blood of a known hematocrit (30%) was applied to the device through the mesh with a positive displacement pipet. The blood was allowed to filter for 1 min. 40 sec. before the device was removed from the paper pad. The pad was then weighed and its hemoglobin content measured with detergent extraction in a pseudo peroxidase assay.

The results are summarized in the following Table I, showing the results with three different blood sample volumes. The membrane devices provided better quality serum than the nylon mesh device. The nylon mesh did not participate in cell filtration.

TABLE I

| | | RECOVERY OF SERUM FROM FILTRATION | | | | | |
|---|---|---|---|---|---|---|---|
| Applied Blood Volume | % Serum Volume To GF Capacity | Gradient Membrane Filterite Membrane | | 1.2μ Membrane | | Nylon Mesh (no membrane) | |
| | | Volume | Hb | Volume | Hb | Volume | Hb |
| 30 μL | 50% | 4.8 μl | .33 mg/mL | 3.2 μl | .18 mg/mL | 4.6, 3.8 μl | 9.0, 3.9 mg/mL |
| 40 μL | 66% | 5.5 μl | .32 mg/mL | 6.1 μl | .34 mg/mL | 10.3, 9.85 μl | 17.1, 35.5 mg/mL |
| 50 μL | 82% | 9.4 μl | .42 mg/mL | 9.8 μl | .40 mg/mL | 12.5, 11.7 μl | 16.4, 49 mg/mL |

A properly functioning blood separation system would show only low concentrations of hemoglobin on the sample pads. The concentration of hemoglobin in the sample pad in a typical commercially available glass fiber system (device type III, nylon mesh) varied from a low of about 3.9 mg/mL of hemoglobin at 30 μL to a high of 49 mg/mL at 50 μL. By comparison, the subject system stayed below about 1 mg/mL over the sample volume range.

II. The Effect of Coating Glass Fiber Filters to Reduce Hemolysis.

Whatman GF/D glass fiber filters were cut into approximately 3"×8" strips, and dipped in a 2% solution of coating agents in deionized water. The filters were then dried at 45° C. for 45 minutes. Double thicknesses of the coated material were placed on a glass plate. A 5 mm disk of chromatography paper was placed beneath the filters to serve as a sample receiving element. Half of the filters were manually compressed to "crush" the fibers, in order to simulate the possible effects of manufacturing processes on the filters. 40 μl of whole blood was then spotted on the filters, and the plasma sample collected on the receiving pad was run in the hemoglobin extraction assay. The sample was run through the filter system, and onto a disk of chromatography paper. This sample disk was then dropped into an extraction reagent (distilled water) to lyse any remaining red blood cells. The amount of hemoglobin remaining in the sample was measured at A405, shown in Table II. A lower reading indicates less hemoglobin present, and therefore decreased hemolysis. While most of the coating agents gave a slight improvement over crushed, untreated filters, it can be seen that treatment with gelatin gave a substantial decrease in hemolysis.

TABLE II

| COATING AGENT (2%) | A405 (NOT CRUSHED) | A405 (CRUSHED) |
|---|---|---|
| untreated | 0.1711 | 0.3058 |
| glycerol | 0.2014 | 0.2606 |
| PVA | 0.2460 | 0.2711 |
| dextran | 0.2260 | 0.3406 |
| PVP | 0.1661 | 0.2324 |
| starch | 0.1868 | 0.2293 |
| gelatin | 0.0657 | 0.0695 |

A titration of gelatin on glass fibers was tested to determine the optimum concentration. Both hemolysis and wetability were evaluated. The filters were prepared as described above, but the concentration of gelatin was varied. The results are shown in Table III.

TABLE III

| % GELATIN | A405 (NOT CRUSHED) | A405 (CRUSHED) | WETABILITY |
|---|---|---|---|
| Untreated | 0.163 | 0.288 | ++++ |
| 0.125% | 0.097 | 0.107 | ++++ |
| 0.250% | 0.078 | 0.093 | ++++ |
| 0.50% | 0.090 | 0.092 | +++ |
| 1.0% | 0.080 | 0.070 | ++ |
| 2.0% | 0.061 | 0.052 | + |

The benefit from a decrease in hemolysis must be weighed against the disadvantage of decreased wetability, where wetability is a measure of how fast a filter hydrates after a sample is applied. At high concentrations of protein the filters tend to become hydrophobic, but at concentrations of 0.125–0.50% gelatin, the filter wetability was excellent and comparable to the control filter, while hemolysis was still significantly reduced compared to the control.

It is evident from the above results that the subject devices allow for production of plasma or serum from blood in a simple manner, where the resulting plasma or serum is free of interfering substances from red blood cells. The sample is quickly produced, taking very little time, requires no technical abilities, and the resulting plasma or serum may then be directly used in an assay for detecting an analyte in the sample. The whole blood sample need not be precisely measured prior to application.

All publications and patent applications mentioned in this specification are indicative of the level of skill of those skilled in the art to which this invention pertains. All publications and patent applications are herein incorporated by reference to the same extent as if each individual publication or patent application was specifically and individually indicted to be incorporated by reference.

Although the foregoing invention has been described in some detail by way of illustration and example for purposes of clarity of understanding, it will be understood that certain changes and modifications may be practiced within the scope of the appended claims.

What is claimed is:

1. A method of separating red blood cells in a blood separation device comprising a depth filter, wherein blood is separated without significant lysis of the cells or freeing of hemoglobin, said method comprising:

adding blood to said depth filter, wherein said depth filter comprises a glass fiber filter having pores in the range of about 1 to $20\mu$ comprising glass fibers of a diameter in the range of about $0.5–9\mu$, a density of about 40 to 200 $g/m^3$ and pre-treated with a solution comprising from about 0.01 to 5% by weight of a fibrous protein, wherein a membrane is in fluid receiving relationship with said depth filter, wherein said membrane is a non-asymmetric membrane and has a porosity in the range of about 0.2 to $7\mu$ or an asymmetric membrane and has a minimum porosity not less than about $0.2\mu$ and a maximum porosity not exceeding about $40\mu$, whereby said blood flows through said device by at least one of capillary action and gravity; and collecting the substantially red-blood-cell- and hemoglobin-free serum or plasma from said device.

2. A method according to claim 1, wherein said fibrous protein is gelatin.

* * * * *